Figure 2:
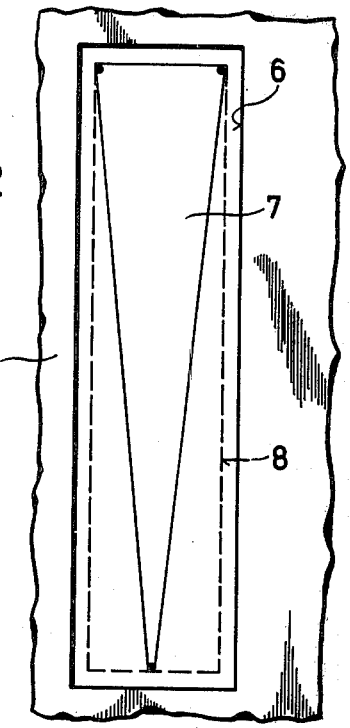

United States Patent [19]

Musaph

[11] 4,163,902
[45] Aug. 7, 1979

[54] X-RAY APPARATUS COMPRISING BEAM SHAPING RESTRICTOR PLATE HAVING KEY-SHAPED GAP

[76] Inventor: Freddy W. Musaph, Tellazamäentie, 04320 Riihikallio, Finland

[21] Appl. No.: 851,059

[22] Filed: Nov. 14, 1977

[30] Foreign Application Priority Data

Dec. 17, 1976 [FI] Finland ................................. 763628

[51] Int. Cl.$^2$ ............................................. A61B 6/00
[52] U.S. Cl. ..................................... 250/482; 250/505
[58] Field of Search ................ 250/482, 520, 471, 505

[56] References Cited

U.S. PATENT DOCUMENTS 2,890,346  6/1959  Kizaur et al. ......................... 250/471

*Primary Examiner*—Alfred E. Smith
*Assistant Examiner*—T. N. Grigsby

*Attorney, Agent, or Firm*—James & Franklin

[57] ABSTRACT

Apparatus for an X-ray device, adapted for use with an X-ray tube, film and an object to be radiated disposed intermediate the tube and the film, comprises a restrictor plate of radiation-opaque material adapted to be disposed intermediate the tube and object and comprising a key-shaped gap configured and dimensioned to shape a beam of radiation passing therethrough from the tube to the object to obtain an advantageous darkness distribution on the film. The gap is preferably shaped like a downwardly converging key. The apparatus may additionally include a cover plate of radiation-opaque material adapted to be disposed intermediate the object and the film and comprising a gap configured and dimensioned to be slightly larger than the beam of radiation passing therethrough from the object to the film to minimize the diffraction of the beam intermediate the cover plate and the film.

4 Claims, 2 Drawing Figures

U.S. Patent    Aug. 7, 1979    4,163,902

X-RAY APPARATUS COMPRISING BEAM SHAPING RESTRICTOR PLATE HAVING KEY-SHAPED GAP

The present invention relates to an apparatus for X-ray device, the purpose of which is to provide better and clearer X-ray radiograph, particularly when the question is about so-called X-ray panoramic image. In X-ray radiography the beam of X-ray radiation is desired to be restricted or limited according to the object to be radiographed. Complete restriction cannot, however, be accomplished and sometimes it is not even possible. When the question is about medical X-ray radiography, the radiation must penetrate through various layers of tissue, the thickness and absorption properties of which vary to a great extent. The intensity of X-ray radiation must, thus, be measured according to the layer the penetration of which is the hardest, which means, of course, that the radiation intensity is unnecessarily powerful on other, more easily penetrable areas. The purpose of the present invention is to provide an apparatus whereby the beam produced by X-ray radiation can be restricted according to the object to be radiated in such a way that there is obtained appropriate radiation intensity in the entire area to be radiographed without using, however, unnecessary over-effect in those areas to be radiographed where it is not needed.

The invention is characterized in that it consists of the restriction plate positioned between the X-ray tube and the object to be radiated comprising a designed gap for a radiation beam in order to accomplish a suitably shaped darkness distribution on the film, in addition to which, there is possibly situated a cover plate in front of the film, the cover plate being provided with a gap slightly larger than the beam. This gap has been preferably designed to form a downwardly converging key. On the other hand, the gap in the cover plate is slightly larger than the perpendicular cross-section of the radiation beam penetrating therethrough. Preferably it corresponds to the shape of the gap of the restrictor.

Figure 1:
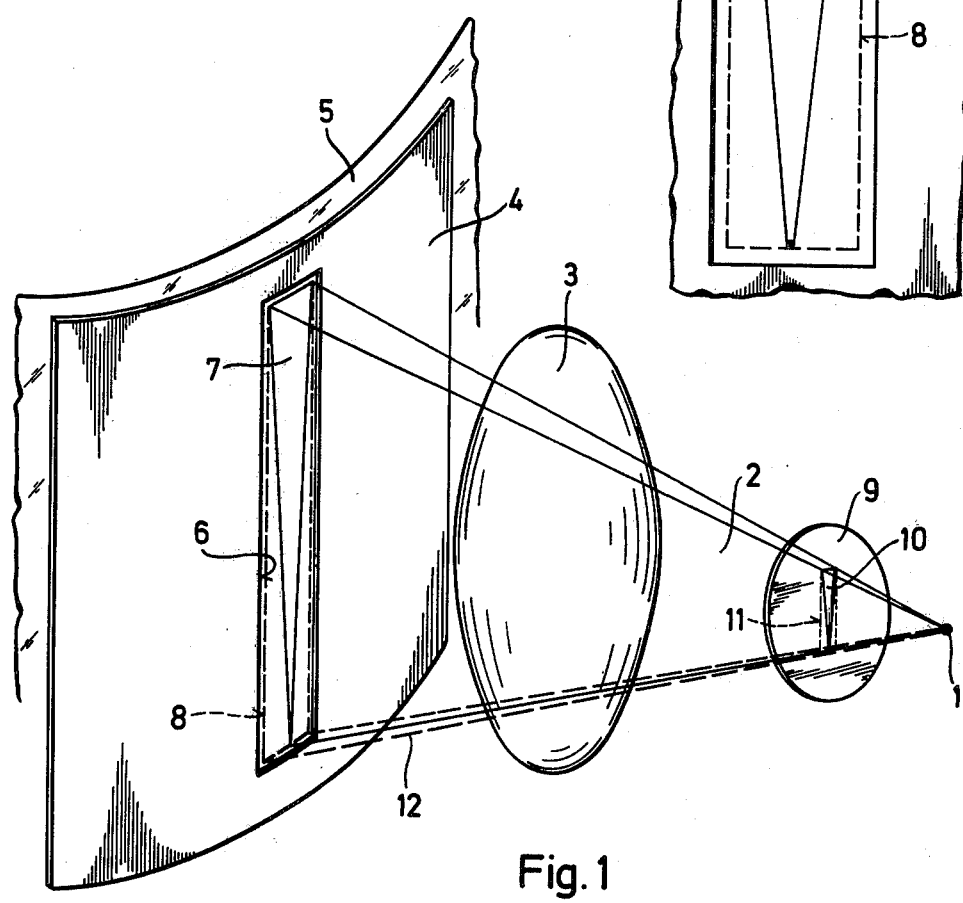

The invention will be explained in more detail with reference to the accompanying drawings, in which:

FIG. 1 presents the principle according to the invention,

FIG. 2 presents the gap in the cover plate.

The apparatus solution according to the invention depicted in the figures is particularly intended for so-called panorama-tomographic radiography by means of which e.g. human teeth can be radiographed by one single radiograph. In such technique the source of radiation is located behind the head and the beam of radiation penetrates from behind through the teeth onto the movable film in front. The source of X-radiation is a kind of spot and the rays are restricted to a beam 2 the cross-section of which is rectangular 8, 11. In the panorama-tomographic case disclosed in the figure, the upper half of the beam must penetrate through a considerably thicker layer of bones, which is of course a lot harder to penetrate as compared to the rays in the lower part of the beam. The intensity used must of course be dimensioned according to this upper layer which is more difficult to penetrate, whereby there must be used unnecessarily high radiation intensity in lower parts of the beam. It is obvious that such unnecessary use of radiation intensity is disadvantageous and unnecessary as far as health is concerned and for advantageous darkness distribution on the film.

To overcome this drawback, in front of the source of radiation 1 there is, according to the invention, located a restrictor 9 provided with a gap 10. This gap 10 is restricted according to the object 3 to be radiated so that the gap will become key-shaped, the tip of said key pointing downwards. In FIG. 1, the unrestricted cross-section of the beam has been depicted by dashed lines at 11. The beam 2, restricted as to its lower part, continues from the restrictor 9 penetrating the object 3 to be radiated, i.e. the patient's head, the radiation intensity being more powerful in the upper part than in the lower part of the object. FIG. 1 despicts, by means of dashed lines 12, the unrestricted lower part of the beam. This actually presents normal practice. The gap 10 of the restrictor plate 9 is designed so as to restrict the lower part of the beam 2 so that on the film 5 there is obtained even or uniform darkness distribution of the entire area to be radiated. In order to obtain satisfactory radiograph a on the film 5, there is a cover plate 4 located in front of it which, in turn, is provided with a gap 6 intended for the beam. Gap 6 in plate 4 is dimensioned to be somewhat larger than the cross-section of the beam of radiation in order to avoid diffraction of the beam behind the plate, the diffraction, in turn, impairing the quality of the image. FIG. 2 shows the gap 6 of the cover plate 4 to an enlarged scale. The figure shows that the gap 6 has been dimensioned to be somewhat larger than the beam 7 going therethrough, the outline of the beam being depicted in FIG. 2. Dashed lines 8 show the outlines of the unrestricted beam. In this event, thus, the gap 6 in plate 4 is rectangular. Preferably it may, however, be of the same shape as the gap 10 in the restrictor 9. The present invention is not restricted to the panorama-tomographic apparatus depicted in the figures but it can be adapted to all kinds of X-ray radiography independent of the object.

I claim:

1. Apparatus for an X-ray device adapted for use with an X-ray tube, a radiation-sensitive film, and an object to be radiated disposed intermediate the tube and the film comprising a restrictor plate of radiation-opaque material comprising a key-shaped gap configured and dimensioned to shape a beam of radiation passing therethrough from the tube to the object to obtain an advantageous darkness distribution on the film.

2. The apparatus of claim 1 wherein said gap is shaped like a downwardly converging key.

3. The apparatus of claims 1 or 2 additionally including a cover plate of radiation-opaque material adapted to be disposed intermediate the object and the film and comprising a gap configured and dimensioned to be slightly larger than the beam of radiation passing therethrough from the object to the film to minimize the diffraction of the beam intermediate said cover plate and the film.

4. The apparatus of claim 3 wherein said cover plate gap is shaped like said restrictor plate gap.

* * * * *